United States Patent [19]

Hounsell

[11] Patent Number: 4,546,086

[45] Date of Patent: Oct. 8, 1985

[54] MICROBIAL CULTURE APPARATUS

[76] Inventor: Melvin W. Hounsell, 6441 Alice La., Rockton, Ill. 61072

[21] Appl. No.: 459,048

[22] Filed: Jan. 19, 1983

[51] Int. Cl.$^4$ .................. C12M 1/00; C12M 1/16; F01C 1/00

[52] U.S. Cl. .................. 435/287; 435/299; 422/236

[58] Field of Search .......... 435/287, 294, 295, 296, 435/297, 298, 299, 300, 301, 801, 807; 422/236

[56] References Cited

U.S. PATENT DOCUMENTS

| | | | |
|---|---|---|---|
| 3,246,959 | 4/1966 | Brewer | 422/236 |
| 3,248,302 | 4/1966 | Mackin | 290/40 F |
| 4,012,203 | 3/1977 | Rosiere | 422/236 |
| 4,013,422 | 3/1977 | Spinner et al. | 422/211 |
| 4,023,934 | 5/1977 | Spinner et al. | 422/86 |
| 4,038,148 | 7/1977 | Miller et al. | 435/296 |
| 4,129,483 | 12/1978 | Bochner | 435/301 |
| 4,246,339 | 1/1981 | Cole et al. | 435/7 |
| 4,347,222 | 8/1982 | Beall et al. | 435/287 |

Primary Examiner—Robert J. Warden
Assistant Examiner—Cynthia Lee Foulke
Attorney, Agent, or Firm—Vernon J. Pillote

[57] ABSTRACT

A microbial culture apparatus including an outer sealable enclosure for receiving a culture retaining container and a self-contained anaerobic gassing and indicator apparatus which can be selectively activated to provide a gaseous atmosphere around the culture retaining container. The gassing and indicator apparatus includes an open top receptacle having a first rupturable container for producing a gaseous atmosphere, a second rupturable container containing a color indicator, and a catalyst, and a cover for the receptacle arranged to rupture both rupturable containers when the cover is moved to a closed position to activate the gassing and indicating apparatus. The outer enclosure comprises an outer open top receptacle for receiving the culture retaining container and the gassing and indicator apparatus, and a cover which can be moved to a closed position sealing the outer receptacle and activating the gassing and indicating apparatus.

11 Claims, 5 Drawing Figures

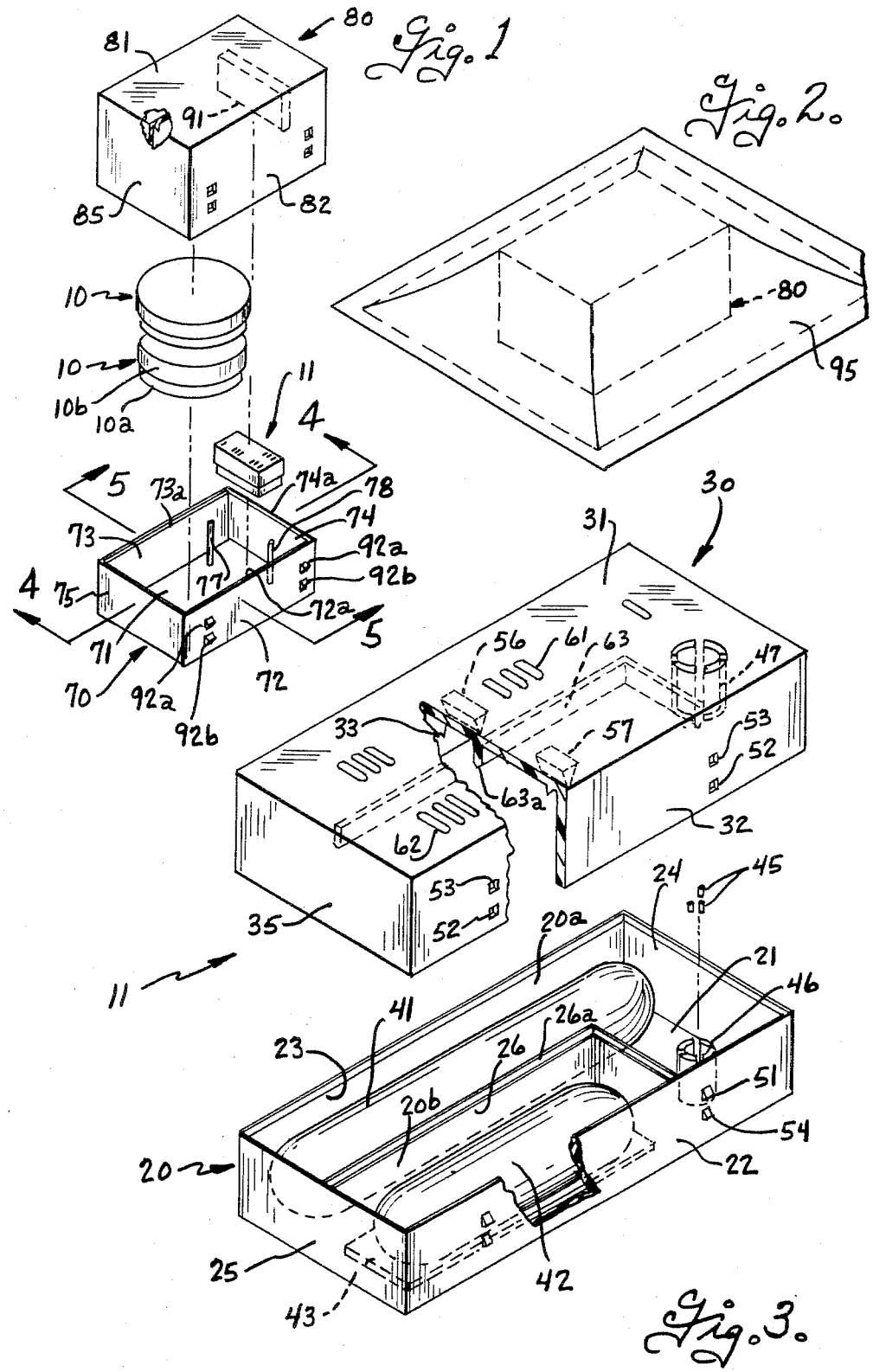

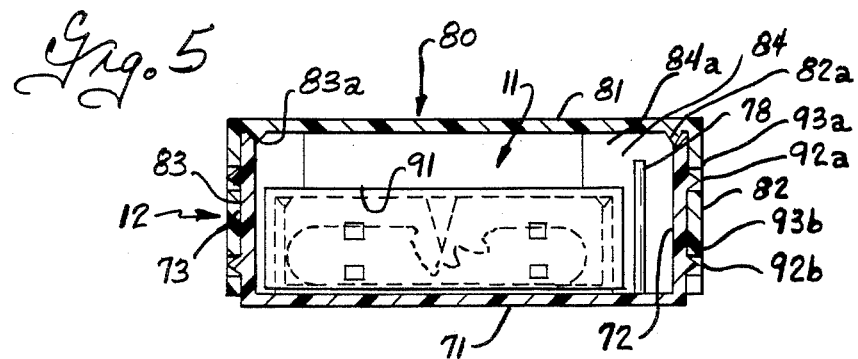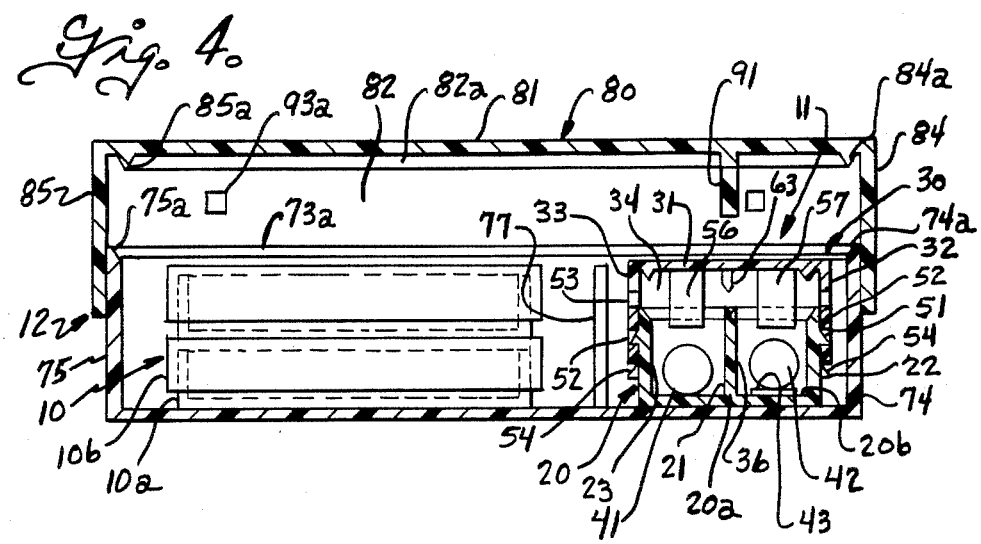

MICROBIAL CULTURE APPARATUS

BACKGROUND OF THE INVENTION

The treatment of many bacterial diseases in man and in lower animals requires the infecting organism to be isolated and identified. While the collecting of such samples generally presents no difficulty, the storage and/or transportation of the sample to the testing laboratory under conditions which require the sample to be viable and free from contamination upon arrival, does present serious problems. It is necessary to not only avoid contamination of the sample from other organisms, but to also provide an environment which will maintain viability of the microbial culture during the time it is being transported and stored prior to being tested in the laboratory. Bacteria of the anaerobic or obligate types such as the bacilli of tetanus, gas gangrene, botulism and bacteroides require an oxygen deficient or oxygen free environment for proper growth and maintenance. Some other organisms require a special gaseous atmosphere for proper growth. Thus, gonococcus, meningococcus and brucella, require a carbon dioxide enriched atmosphere for proper growth.

Microbial samples are sometimes cultured in a separate culture retainer container such as a conventional petri dish or a culture tube or tubes containing a suitable nutrient medium. U.S. Pat. No. 3,248,302 discloses a petri dish in which the lid has a membraneous sealing flange arranged to form a seal with the dish when the lid is closed, and a capsule containing a reducing agent or other chemicals or agents for use in effecting oxygen absorption or desired atmospheric conditions in the petri dish. Such an arrangement requires special care and handling in order to prevent contamination of the culture and nutrient medium by the reducing agent or other chemicals or agents used in effecting oxygen absorption or other atmospheric conditions in the petri dish. U.S. Pat. No. 3,246,959 discloses a rigid outer vessel of a size to receive a culture retaining container such as a petri dish, and a gas generating apparatus which can be selectively activated and deposited in the outer vessel before it is closed and sealed, to provide a selected gaseous atmosphere around the culture retaining container. The arrangement disclosed in this patent, however, requires activation of the gas generating means and depositing of the same in the outer vessel before the latter can be closed and sealed. U.S. Pat. Nos. 4,012,203; 4,013,422; 4,023,934 and 4,038,148 disclose a flexible bag or package which is adapted to receive a separate culture retaining container such as a petri dish or culture tubes, together with a gas generating means and/or a gas indicator means. The flexible bags or packages do not retain the several components in a definite position in the bag. Further, these apparatus require separate operations to close the flexible bag or package and to activate the gas generating apparatus and/or gas indicator apparatus. Further, the flexible bags or packages do not protect the culture retaining container against damage from impact or crushing. Further, these culture apparatus utilize a deformable tube type housing for the gas generating apparatus and color indicator apparatus and which required assembly of several components in predetermined sequence through an end of the tube. This increased the cost and the time in assembly of the generating apparatus and color indicator apparatus. In addition, the flexible tube used for housing the gas generator and color indicator are sometimes punctured by a fragment or shard of the glass ampoule in the tube when the ampoule is ruptured. Puncturing of the tube can not only cause injury to the user, but can also result in puncturing of the outer flexible package with consequent loss of the atmospheric sustaining integrity of the outer package.

SUMMARY OF THE INVENTION

Although the prior art discloses microbial culture apparatus which can be selectively activated to provide a gaseous environment around a culture retaining container, there is a need for a microbial culture apparatus which is more convenient, economical and efficient to produce and use.

According to one aspect of the present invention, there is provided a microbial culture apparatus for providing an anaerobic gaseous atmosphere around a culture retaining container comprising an anaerobic gassing and indicator apparatus including an open top receptacle having a bottom wall and upstanding side wall means, a cover having a top wall and depending flange means adapted to extend downwardly along the side wall means of the receptacle, partition means in the receptacle defining a first open top compartment at one area of the bottom wall and a second open top compartment at a second area of the bottom wall, a first rupturable container in the first compartment containing a material for use in providing a gaseous atmosphere, a second rupturable container in the second compartment containing a redox color indicator liquid, interengaging detent means on the receptacle side wall means and cover flange means for releasably retaining the cover in a first position on the receptacle with the top wall of the cover spaced above the partition wall means of the receptacle a distance to retain the first and second containers in their respective first and second compartments without rupturing the containers, the interengaging detent means being releasable in response to downward pressure on the cover to allow the cover to move down to a second position on the receptacle, means operative in response to the movement of the cover from its first to its second position on the receptacle for rupturing the first and second rupturable containers, vent means for venting the first and second compartments when the cover is in its second position, and outer enclosure means for providing a sealable enclosure around the culture retaining container and the anaerobic gassing and indicator apparatus.

According to another aspect of the present invention, the outer sealable enclosure includes a second receptacle having a bottom wall and upstanding side wall means and of a size to receive the anaerobic gassing and indicator apparatus at one area of the bottom wall and to receive a culture retaining container at another area of the bottom wall, a second cover having a top wall and depending flange means adapted to extend downwardly along the side wall means of the second receptacle, interenging detent means on the side wall means of the second receptacle and flange means of the second cover for releasably retaining the second cover in a first position on the second receptacle with the top wall of the second cover spaced above the bottom wall of the second receptacle a distance to retain the anaerobic indicator apparatus at said one area of the bottom wall of the second receptacle without depressing the first cover on the anaerobic gassing and indicator apparatus, the second interengaging detent means being releasable in response to downward pressure on the second cover to allow the second cover to be moved down to a second position, means responsive to movement of the second cover from its first position to its second position for depressing the first cover on the anaerobic gassing and indicator apparatus sufficient to move the latter to its second position, and means on the second cover and second receptacle engageable when the second cover is in its second position for sealing the second cover to the second receptacle.

The anaerobic culture apparatus can be more easily and economically assembled since the various components can be positioned in the respective compartments through the open top of the receptacle. The microbial culture apparatus is also easier to use since it can be closed and activated in a single operation by pressing the cover down to its second position, thereby rupturing the rupturable containers and sealing the compartments. In addition, the anaerobic culture apparatus effectively avoids the problem sometimes encountered with prior microbial culture apparatus of the type in which the ampoules are housed in a flexible plastic tube so they can be ruptured by squeezing the tube, and wherein shards or pieces of the ampoules sometimes pierce the tube and cause injury to the user and loss of the atmosphere retaining integrity of the tube.

These, together with other objects, features and advantages of this invention will be more readily understood by reference to the following detailed description when taken in conjunction with the accompanying drawings wherein:

FIG. 1 is an exploded perspective view of a microbial culture apparatus embodying the present invention;

FIG. 2 is a perspective view of a package for transporting the microbial culture apparatus;

FIG. 3 is an exploded perspective view of an anaerobic gassing and indicator apparatus forming a part of the microbial culture apparatus;

FIG. 4 is a sectional view taken on the plane 4—4 of FIG. 1 and illustrating the microbial culture apparatus assembled and prior to activation;

FIG. 5 is a transverse sectional view taken on the plane 5—5 of FIG. 1 and illustrating the microbial culture apparatus after it has been activated.

The microbial culture apparatus is arranged to maintain a suitable gaseous atmosphere around one or more culture retaining containers during storage and/or transport of the cultures. The culture retaining containers shown herein are conventional petri dishes 10 each having a bottom 10a and a cover 10b which fits sufficiently loosely on the bottom to allow passage of a gaseous atmosphere into and out of the petri dish when the cover is positioned on the bottom. The microbial culture apparatus can also be adapted for use with other separate culture retaining containers such as a culture tube or tubes. As is well known in the art, culture sustaining medium appropriate for the particular microbial culture or cultures to be stored or transported, is commonly provided in the culture retaining container. In general, the microbial culture apparatus includes a self-contained anaerobic gassing and indicating apparatus 11 which can be selectively activated to provide a suitable gaseous atmosphere and to indicate the presence or absence of oxygen, and an outer enclosure 12 for receiving the culture retaining container 10 and the anaerobic gassing and indicating apparatus and arranged to provide a sealed enclosure therefor.

The anaerobic gassing and indicating apparatus 11 includes an open top receptacle 20 having a bottom wall 21, upstanding side walls 22, 23, and end walls 24, 25. A cover 30 has the top wall 31 dimensioned to overlie the top of the receptacle and depending side flanges 32, 33 and end flanges 34, 35 adapted to extend downwardly along the side walls of the receptacle. The receptacle and cover are conveniently formed by molding of a rigid polymer or co-polymer, for example Nylon, polycarbonate or polystyrene, to provide a shape sustaining receptacle and cover, and the cover is preferably formed of a transparent material.

Divider means, preferably in the form of an imperforate partition wall 26, is provided in the receptacle to divide the same into a first compartment 20a at one area of the bottom wall 21 and a second compartment 20b at a second area of the bottom wall. A means for providing a preselected gaseous atmosphere is provided in the compartment 20a, and a means for indicating the presence or absence of oxygen is provided in compartment 20b. The means for providing a gaseous atmosphere can be a gas generating apparatus which includes a solid gas generating material and a liquid in a rupturable container for reacting with the solid gas generating material to produce the desired gaseous atmosphere, for example as disclosed in U.S. Pat. Nos. 4,012,203 and 4,013,422 to which reference is made for a more detailed disclosure. A rupturable container 41 containing a material for use in providing a desired gaseous atmosphere, is positioned in the compartment 20a. If a gas generating apparatus is used, then the rupturable container would contain a liquid which is reactive with a solid gas generating material (not shown) in the compartment 20a, to produce the desired gas. However, solid gas generating materials are generally deliquescent and, to avoid the problems encountered with deterioration of the solid gas generating material prior to use, the container 41 preferably includes the gas or mixture of gasses under pressure which, when released, will directly produce the desired gaseous atmosphere. The container may, for example, contain a reducing gas such as hydrogen or acetylene, or a reducing gas in combination with a culture sustaining gas such as carbon dioxide. The container 41 can be formed of a rupturable glass or plastic, or of a thin metal which can be punctured, or it can be a rigid container having at least one area or plug which is rupturable as by puncturing or piercing. The means for indicating the presence or absence of oxygen includes a rupturable container 42 containing a redox color indicator liquid positioned in the compartment 20b. The redox color indicator liquid may be selected from any suitable material which will reversibly change color when the atmosphere around it changes from one whch is oxygen deficient to one where there is a significant or substantial amount of oxygen in the atmosphere and vice versa. The color indicator liquid may, for example, be a 0.001% solution of resazurin in water. This indicator is colorless in an oxygen free atmosphere and is pink in an oxygen containing atmosphere. The container 42 may be an ampoule of glass or of plastic which is rupturable when compressed. An absorbent pad 43 of a non-woven polyester material is provided for absorbing the color indicator when the ampoule is ruptured and preferably underlies the ampoule in the compartment 20b. The size of the rupturable container 42 for the color indicator liquid will generally be smaller than the size of the container 41 for the gassing material and the partition 26 is advantageously formed with a generally L-shaped configuration as best shown in FIG. 3 so that the compartment 20a is substantially longer than the compartment 20b.

A catalyst is advantageously provided for inducing the reaction of the reducing gas with oxygen. A 5% palladium-on-alumina catalyst may be used, although other catalysts which induce a reducing gas to react with oxygen at room temperature may be employed. The catalyst, which is preferably in the form of one or more small porous pellets 45, is maintained in a small catalyst chamber 46 that communicates with the compartment 20a. The catalyst chamber is formed integrally with the receptacle and, in order to facilitate molding, is preferably in the form of a segmented upright cylinder that is open at its top and with the spaces between the segments defining vent passages to communicate the catalyst chamber with the compartment 20a. A means is provided on the cover for retaining the catalyst pellets in the catalyst chamber. The catalyst retaining means is conveniently formed integrally with the cover and, to facilitate molding, is in the form of a segmented cylindrical sleeve 47 arranged to telescopically engage the catalyst chamber 46; to allow vertical movement of the cover while retaining the catalyst pellets in the catalyst chamber. The slots between the segments in the retainer sleeve 47 are arranged to register with the slots in the catalyst chamber 46 to maintain open communication between the catalyst chamber and the compartments when the cover is closed.

Interengaging detents, including protrusions 51 on the outer side of the side walls of the receptacle and sockets 52 on the side flanges of the cover, are provided for releasably supporting the cover in a first position in which the top wall is spaced above the upper edges of the side walls of the receptacle as shown in FIGS. 1 and 4. The interengaging detents are releasable in response to downward pressure on the cover to allow the cover to move down to a second position in which a top wall of the cover is contiguous to the edge of the side walls of the receptacle as shown in FIG. 5. A second set of sockets 53 are provided on the side flanges of the cover to receive the protrusions 51 on the side walls of the receptacle when the cover is moved to its second position, to thereby retain the cover in that position. A second set of protrusions 54 are conveniently provided on the side walls of the receptacle below the protrusions 51 at locations to engage the sockets 52 on the side flanges of the cover when the cover is in its second position, to aid in holding the cover in its second position. As shown in FIGS. 3 and 4, the protrusions 51 and 54 each have a downwardly and outwardly inclined upper face to cam the side flanges on the cover outwardly when the cover is pressed down, and the lower faces of the protrusions extend generally transverse to the side walls to retain the cover against upward movement. Punches 56 and 57 are provided on the underside of the cover for rupturing the containers 41 and 42 respectively, when the cover 30 is moved from its first to its second position. The punches extend downwardly from the cover a distance such that they are spaced above the rupturable containers 41 and 42 when the cover is in its first position as shown in FIG. 4, and they engage the respective rupturable containers when the cover is moved to its second position to rupture the same as shown in FIG. 5. The shape and configuration of the punches will vary with the type of rupturable container utilized. In the embodiment shown, the punches 56 and 57 have a generally wedge shaped configuration with the apex of the wedge extending crosswise of the respective rupturable container. If one of the rupturable containers such as the container 41 is formed of a thin metal or other material that can be ruptured by piercing, then the punch can be formed with a sharpened point for puncturing or piercing the rupturable container.

Provision is made for venting the compartments 20a and 20b to the surrounding atmosphere when the cover is in its second position. As shown in FIG. 3, vent openings 61 and 62 are provided at least in the cover 30 at locations to vent the compartments 20a and 20b to the surrounding atmosphere. The compartments 20a and 20b are preferably sealed from direct communication with each other, when the cover is in its second or closed position. For this purpose, a rib 63 is provided on the underside of the cover at a location to register with the partition wall 26, and the rib has a generally V-shaped apex 63a arranged to project into a V-shaped notch 26a in the upper edge of the partition wall, when the cover is in its closed position. A resilient sealing compound (not shown) may be applied as a thin coating on the V-shaped surface 26a, to enhance the seal between the rib and projection wall 26.

The anaerobic gassing and indicator apparatus 11 can be used in a rigid type sealable outer enclosure such as the anaerobic jar shown in U.S. Pat. No. 3,246,959 or in a flexible bag type outer enclosure such as shown in U.S. Pat. Nos. 4,023,934 and 4,038,148. However, the anaerobic jar shown in U.S. Pat. No. 3,246,959 requires activation of the anaerobic gassing apparatus before closing and sealing the outer enclosure. If used in a flexible bag type outer enclosure of a type shown in U.S. Pat. Nos. 4,023,934 and 4,038,148, the anaerobic gassing and indicator apparatus can be activated after the bag is closed by pressing on the bag in the area where the gassing and indicator apparatus is positioned. However, flexible bag type outer enclosures do not protect the culture retaining container against damage from impact or crushing during transport. Further, the flexible bag type outer enclosure inflates and presents a very large volume, thus requiring a gas producing apparatus of relatively large capacity.

An improved outer enclosure 12 is provided which includes a receptacle 70 having a bottom wall 71, upstanding side walls 72 and 73 and end walls 74 and 75. The receptacle 70 is made sufficiently large to receive one or more separate culture retaining containers 10 such as a petri dish at one area of the bottom wall 71, and to receive the anaerobic gassing and indicator apparatus 11 at a second area of the bottom wall. Locating pins 77 and 78 are provided on the bottom wall at locations to engage the anaerobic gassing and indicator apparatus 11 and maintain it in a predetermined area of the bottom wall 71. A cover 80 has a top wall 81 dimensioned to overlie the top of the receptacle, depending side flanges 82 and 83, and end flanges 84 and 85.

The cover is arranged so that it can be pressed down onto the receptacle to simultaneously activate the anaerobic gassing and indicator apparatus 11 and to seal the cover 80 to the receptacle 70 and form a sealed enclosure around the culture retaining container and gassing and indicator apparatus. The upper edges of the side walls 72, 73 and end walls 74, 75 are formed with beveled surfaces 72a–75a respectively. The underside of the top wall 81 is provided with ribs 82a–85a that are spaced inwardly from the flanges 82–85 respectively and formed with beveled surfaces at their outer side generally complementary to the respective beveled surfaces 72a–75a on the side and end walls of the receptacle to engage and form a seal therewith when the cover is closed. A resilient sealing compound (not shown) such as a resilient rubber or plastic compound is advantageously applied as a thin coating on the surfaces 72a–75a to enhance the seal between the cover and receptacle. An anvil 91 is provided on the underside of the cover 80 at a location to engage and depress the cover 30 on the anaerobic gassing and indicator apparatus 11 when the outer cover 80 is pressed down to its closed position as shown in FIG. 5. The anvil 91 dimensioned so that, when the outer cover is moved to its second position on the outer receptacle, the anvil depresses the cover 30 on the gassing and indicator apparatus and moves the latter down to its second position to rupture the containers 41 and 42. Thus, pressing the cover 80 down to its closed position on the outer receptacle 70, simultaneously activates the gassing and indicator apparatus 11 and seals the outer cover to the outer receptacle to form a sealed enclosure around the culture retaining container 10 and gassing and indicator apparatus 11.

Means are advantageously provided for releasably locking the outer cover in its closed position on the receptacle. For this purpose, sets of protrusions 92a and 92b are provided on the outer sides of the side walls of the receptacle 70 and arranged to engage sockets 93a and 93b in the side flanges on the cover, when the cover is in its closed position as shown in FIG. 5. The protrusions 92a and 92b are preferably formed with a downwardly and outwardly inclined upper surface to cam the side flanges on the cover outwardly when the cover is pressed downwardly until the protrusions extend into the sockets. The underside of the protrusions 92a and 92b can be inclined upwardly as shown in FIG. 5, to facilitate removal of the cover 80 from the receptacle 70 without having to break or otherwise damage or destroy the outer enclosure. The protrusions and sockets are also advantageously arranged to releasably support the cover 80 in a first or raised position on the receptacle 70 in which the top wall of the cover 80 is spaced above the upper edges of the receptacle as shown in FIG. 4. Thus, the detents 92a are adapted to extend into the sockets 93b on the cover to releasably support the cover in its raised position shown in FIG. 4.

The anaerobic gassing and indicator apparatus 11 is preassembled with the rupturable containers 41 and 42, pad 43 and catalyst 45 in their respective compartments and chambers, and the cover 30 is positioned on the receptacle 20 in a first or raised position as shown in cross section in FIG. 4, with the cover 30 spaced above the top of the receptacle. The anaerobic gassing and indicating apparatus can be packaged separately in an outer wrapper or bag and sterilized. Preferably, the anaerobic gassing and indicating apparatus is preassembled in the outer receptacle, with or without a culture retaining container 10, and the outer cover 80 then positioned on the outer receptacle in a first or raised position as shown in FIG. 4, to retain the gassing and indicating apparatus in its position in the outer receptacle.

The assembled culture apparatus is preferably sterilized and shipped in a sterile condition in a bag or wrapper shown at 95 in FIG. 2. The wrapper 95 is conveniently formed with a back sheet of a gas permeable material such as glassine, craft paper or Tyvek, and a top sheet of the same material or a clear low gas permeable film or sheet material which is bound to the edge of the back sheet material, both sheets being of a suitable porosity to maintain product sterility. By utilizing a gas permeable sheet for at least one of the sides of the wrapper or package 95, the culture apparatus can be sterilized after sealing of the wrapper by subjecting the sealed wrapper to a sterilizing gas such as ethelyne oxide. Alternatively, the culture apparatus and package can be sterilized by radiation or by inserting the culture apparatus into an opening in the bag which is gas sterilized prior to sealing.

From the foregoing, it is thought that the construction and manner of use of the apparatus will be readily understood. The culture apparatus is fully assembled and ready for use with the outer cover 80 in its raised position when the culture apparatus is removed from the wrapper or package 95. The outer cover 80 is removed from the outer receptacle 70 and, after a culture retaining container 10 having a culture therein has been positioned in the outer receptacle, the cover 80 is reapplied and pressed down to a second or closed position as shown in FIG. 5 to form a sealed enclosure. The anvil 91 on the outer cover engages the cover 30 on the gassing and indicator apparatus and moves the latter to its second or lower position as shown in FIG. 5. The punches on the cover of the gas and indicator apparatus rupture the respective containers 41 and 42. The gas produced by rupturing of container 41 passes out through vent openings 61 into the outer receptacle and gas from the outer receptacle can in turn pass back through some of the openings 61 into the compartments 20a and 20b. If the gas released by the rupturing of the container 41 contains a reducing gas, the reducing gas will catalytically react with any oxygen entering the compartment 20a to produce water. Rupturing of the color indicator container 42 releases the color indicator liquid which is absorbed in the pad 43 to indicate by color change the presence or absence of oxygen.

The embodiments of the invention in which an exclusive property or privilege is claimed are defined as follows:

1. A microbial culture apparatus for providing an anaerobic gaseous atmosphere around a culture retaining container comprising, an anaerobic gassing and indicator apparatus including an open top receptacle having a bottom wall and upstanding side wall means, a cover having a top wall and depending flange means adapted to extend downwardly along the side wall means of the receptacle, partition means in the receptacle defining a first open top compartment at one area of the bottom wall and a second open top compartment at a second area of the bottom wall, a first rupturable container in the first compartment containing material for providing a gaseous atmosphere, a second rupturable container in the second compartment containing a redox color indicator liquid, interengaging detent means on the receptacle side wall means and cover flange means for releasably retaining the cover in a first position on the receptacle with the top wall of the cover spaced above the partition wall means of the receptacle a distance to retain the first and second containers in their respective first and second compartments without rupturing the containers, the interengaging detent means being releasable in response to downward pressure on the cover to allow the cover to move down to a second position on the receptacle, means operative in response to movement of the cover from its first to its second position on the receptacle for rupturing said first and second rupturable containers, vent means for venting the first and second compartments when the cover is in its second position, and outer enclosure means for providing a sealed enclosure around a culture retaining container and the anaerobic gassing and indicator apparatus.

2. A microbial culture apparatus according to claim 1 wherein the material in the first container provides at least a reducing gas, wall means in the receptacle defining an open top catalyst chamber communicating with said first compartment, at least one catalyst pellet in the catalyst chamber which promotes reaction between the reducing gas and oxygen, and means on the cover cooperable with the wall means defining a catalyst chamber for maintaining the catalyst pellet in the catalyst chamber when the cover is in its first and its second positions.

3. A microbial culture apparatus according to claim 1 wherein said material in said first container is gas.

4. A microbial culture apparatus according to claim 1 including means on the cover engageable with the partition means when the cover is in its second position, for inhibiting direct communication between the first and second compartments.

5. A microbial culture apparatus according to claim 1 wherein said partition means includes a partition wall extending upwardly from the bottom wall, said top wall of said cover has a rib on the underside vertically aligned with said partition wall, and means on the partition wall and rib adapted to engage when the cover is in its second position to inhibit direct communication between the first and second compartments.

6. A microbial culture apparatus for providing an anaerobic gaseous atmosphere around a culture retaining container comprising
  (a) an anaerobic gassing and indicator apparatus including a first open top receptacle having a bottom wall and upstanding side wall means, a first cover having a top wall and depending flange means adapted to extend downwardly along the side wall means of the first receptacle, divider means in the first receptacle defining a first open top compartment at one area of the bottom wall and a second open top compartment at a second area of the bottom wall of the first receptacle, a first rupturable container in the first compartment containing material for providing a gaseous atmosphere, a second rupturable container in the second compartment containing a redox color indicator liquid, first interengaging detent means on the side wall means of the first receptacle and flange means of the first cover for releasably retaining the cover in a first position on the first receptacle with the top wall of the cover spaced above the divider means of the receptacle a distance to retain the first and second rupturable containers in their respective first and second compartments without rupturing the first and second rupturable containers, the first interengaging detent means being releasable in response to downward pressure on the first cover to allow the cover to move down to a second position on the first receptacle, means operative in response to movement of the first cover from its first to its second position on the first receptacle for rupturing said first and second rupturable containers, and vent means for venting the first and second compartments when the first cover is in its second position,
  (b) outer enclosure means including a second receptacle having a bottom wall and upstanding side wall means and of a size to receive said anaerobic gassing and indicator apparatus at one area of the bottom wall and to receive a culture retaining container at another area of the bottom wall, a second cover having a top wall and depending flange means adapted to extend downwardly along the side wall means of the second receptacle, second interengaging detent means on the side wall means of the second receptacle and flange means of the second cover for releasably retaining the second cover in a first position on the second receptacle with the top wall of the second cover spaced above the bottom wall of the second receptacle a distance to retain said anaerobic gassing and indicating apparatus at said one area of the bottom wall of the second receptacle without depressing the first cover on the anaerobic gassing and indicating apparatus, the second interengaging detent means being releasable in response to downward pressure on the second cover to allow the second cover to move down to a second position, means responsive to movement of the second cover from its first to its second positions for depressing the first cover on the anaerobic gassing and indicator apparatus sufficient to move the latter to its second position, and means on the second cover and the second receptacle engageable when the second cover is in its second position for sealing the second cover to the second receptacle.

7. A microbial culture apparatus according to claim 6 wherein the material in the first container provides at least a reducing gas, wall means in the first receptacle defining an open top catalyst chamber communicating with said first compartment, at least one catalyst pellet in the catalyst chamber which promotes reaction between the reducing gas and oxygen, and means on the cover cooperable with the wall means defining a catalyst chamber for maintaining the catalyst pellet in the catalyst chamber when the first cover is in its first and its second positions on the first receptacle.

8. A microbial culture apparatus according to claim 6 wherein said material in said first container is a gas.

9. A microbial culture apparatus according to claim 6 wherein the divider means in the first receptacle includes partition wall means extending upwardly from the bottom wall, means on the first cover engageable with the partition wall means when the first cover is in its second position, for inhibiting direct communication between the first and second compartments in the first receptacle.

10. A microbial culture apparatus according to claim 6 wherein said divider means in the first receptacle comprises partition wall means extending upwardly from the bottom wall, said top wall of said first cover having a rib on the underside vertically aligned with said partition wall means, and means on the partition wall means and rib adapted to engage when the first cover is in its second position to inhibit direct communication between the first and second compartments in the first receptacle.

11. A microbial culture apparatus according to claim 6 wherein said last mentioned means includes a beveled surface along the inner side of the upper edge of the side wall means on the second receptacle, the second cover having a rib at the underside of its top wall spaced inwardly from its flange means and having a beveled surface along the outer face of the rib engageable with the beveled surface on the side wall means of the second receptacle when the second cover is in its second position.

* * * * *